(12) United States Patent
Rohringer et al.

(10) Patent No.: US 6,331,626 B1
(45) Date of Patent: Dec. 18, 2001

(54) TRIAZINYLAMINOSTILBENE COMPOUNDS

(75) Inventors: Peter Rohringer, Schönenbuch (CH);
André Geoffroy, Habsheim (FR);
Andreas Burkhard, Basel (CH);
Erwin Marti, Basel (CH); Werner Schreiber, Basel (CH); Josef Zelger, Riehen (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/666,768

(22) Filed: Sep. 21, 2000

Related U.S. Application Data (62) Division of application No. 09/081,427, filed on May 19, 1998, now Pat. No. 6,153,122.

(30) Foreign Application Priority Data

May 23, 1997 (GB) .................................. 9710569.6

(51) Int. Cl.$^7$ .................... C07D 251/70; C09K 11/06; C11D 3/42
(52) U.S. Cl. ................. 544/193.2; 8/919; 8/119; 252/301.21; 252/301.23
(58) Field of Search .......................... 544/193.2

(56) References Cited

U.S. PATENT DOCUMENTS

| | | |
|---|---|---|
| 3,925,260 | 12/1975 | Tscharner et al. ............ 252/543 |
| 4,271,036 | 6/1981 | Uhl et al. ................. 252/301.23 |
| 4,326,982 | 4/1982 | Neumann et al. .......... 252/301.23 |
| 5,076,968 | 12/1991 | Fringeli et al. ............... 252/543 |
| 5,437,818 | 8/1995 | Ehlis et al. ............... 252/301.21 |

FOREIGN PATENT DOCUMENTS

| | | |
|---|---|---|
| 1293804 | 10/1972 | (GB) . |
| 1317465 | 5/1973 | (GB) . |
| 1355218 | 6/1974 | (GB) . |

*Primary Examiner*—Richard L. Raymond
*Assistant Examiner*—Venkataraman Balasubramanian
(74) *Attorney, Agent, or Firm*—Kevin T. Mansfield (57) ABSTRACT

The present invention provides a hydrate of the 4,4'-di-triazinylamino-2,2'-di-sulfostilbene compound having the formula:

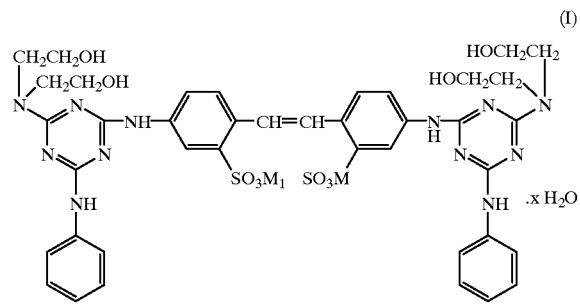

(I)

in which M and $M_1$ independently represent hydrogen, an alkaline-, an alkaline earth metal or ammonium, x is a number within the range of from 1 to 30, and the crystal form of the hydrate (I) being characterised by an X-ray diffraction pattern which is essentially as set out in the accompanying FIGS. 1 to 11; or a mixture containing one or more of the hydrates of the 4,4'-di-triazinylamino-2,2'-di-sulfostilbene compound having the formula (I); processes for the preparation of the new hydrates; and the use of the new hydrates for the preparation of concentrated aqueous formulations of fluorescent whitening agents.

20 Claims, 11 Drawing Sheets

TRIAZINYLAMINOSTILBENE COMPOUNDS

This is a divisional of application Ser. No. 09/081,427, filed on May 19, 1998, now U.S. Pat. No. 6,153,122.

The present invention relates to the novel hydrates of the salts of a specific 4.4'-di-triazinylamino-2,2'-di-sulfostilbene compound, characterised by their water of hydration content; to the crystal forms which are associated with the new hydrates and which are characterised by their X-ray diffraction pattern; to processes for the preparation of the new hydrates; and to the use of the new hydrates for the preparation of concentrated formulations of fluorescent whitening agents.

According to recent practice, fluorescent whitening agents are preferably put on the market in the form of aqueous solutions or suspensions. To this end, for example, the moist filtercakes or dry powders of the fluorescent whitening agents are suspended in water. Dispersants and thickeners are added to the suspension in order to increase the homogeneity, wettability and shelf life of the suspension. Frequently, an electrolyte is also added together with these auxiliaries. Despite the presence of these additives, there are concentration limits for the fluorescent whitening agent suspension, above which the suspension is often unstable on storage and has poor metering characteristics. These concentration limits are often difficult to reproduce, since they can be affected by the nature of a pretreatment which may have been applied to the suspension of the fluorescent whitening agent. In particular, depending on the nature of a pretreatment, a variety of hydrates of the fluorescent whitening agent, having different crystal forms, may be obtained.

Surprisingly, it has now been found that formulations of a specific fluorescent whitening agent, which have an active substance concentration of more than 30% by weight, which are stable on storage and the viscosity of which can be selectively set at a value within a wide range, can be prepared if a specific hydrate or mixtures of hydrates of the fluorescent whitening agent used, having a specific crystal form, or several specific crystal forms, are present. The new formulations contain only low amounts of formulation auxiliaries and are useful for the fluorescent whitening of a wide range of substrates, including textiles and paper.

Accordingly, the present invention provides a hydrate of the 4,4'-di-triazinylamino-2,2'-di-sulfostilbene compound having the formula:

(I)

in which M and $M_1$ independently represent hydrogen, an alkaline-, an alkaline earth metal or ammonium, x is a number within the range of from 1to 30, and the crystal form of the hydrate (I) being characterised by an X-ray diffraction pattern which is essentially as set out in the accompanying FIGS. 1 to 11; or a mixture containing one or more of the hydrates of the 4,4'-di-triazinylamino-2,2'-di-sulfostilbene compound having the formula (I).

Preferred hydrates of formula (I) are compounds in which M and $M_1$ both represent hydrogen or sodium, the hydrates being characterised by an X-ray diffraction pattern which is essentially as set out in the accompanying FIGS. 1 to 7; or a mixture containing one or more of the hydrates of the di-sodium salt of the 4,4'-di-triazinylamino-2,2'-di-sulfostilbene compound having the formula (I).

Figure 8:
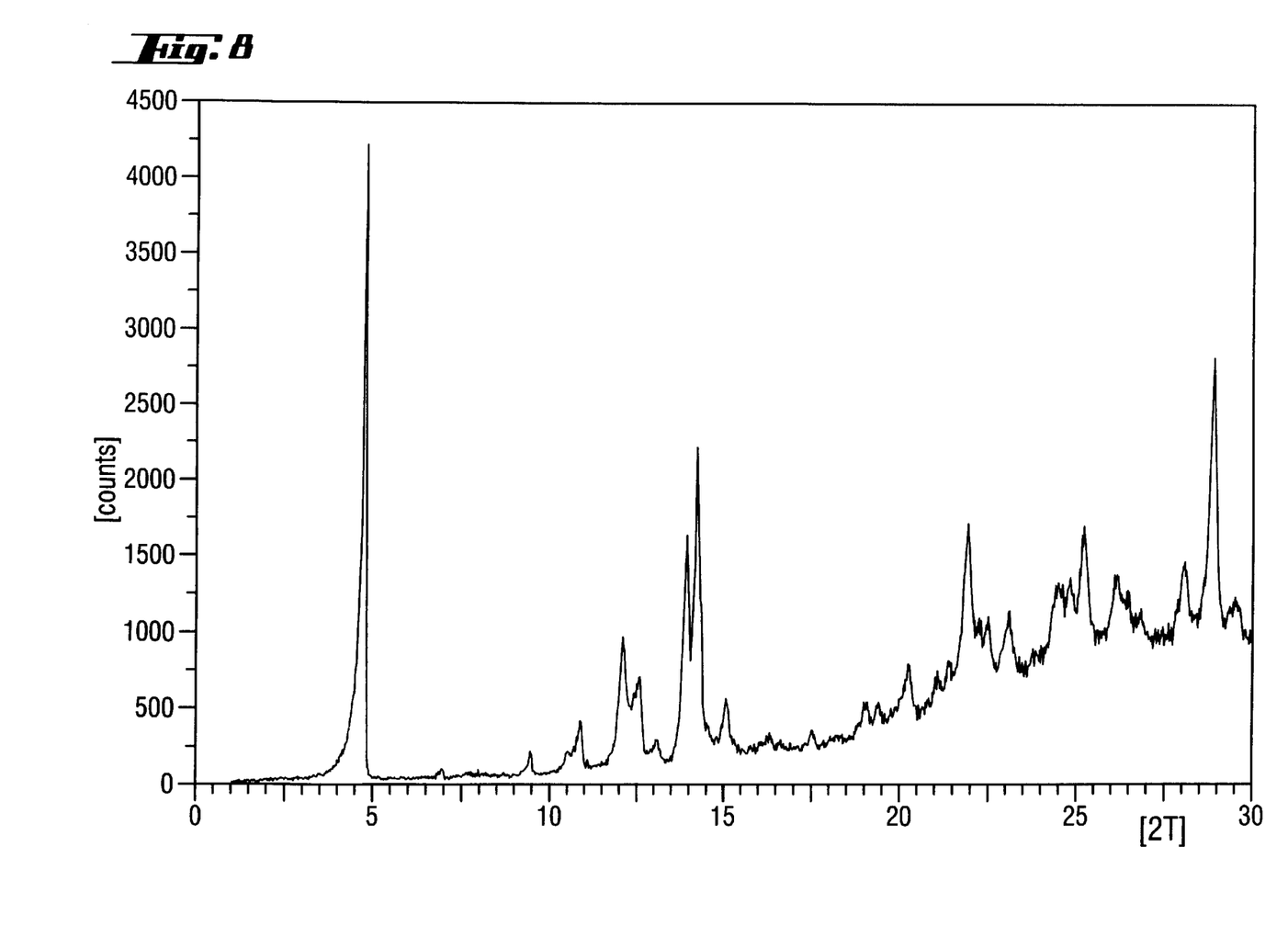
Figure 9:
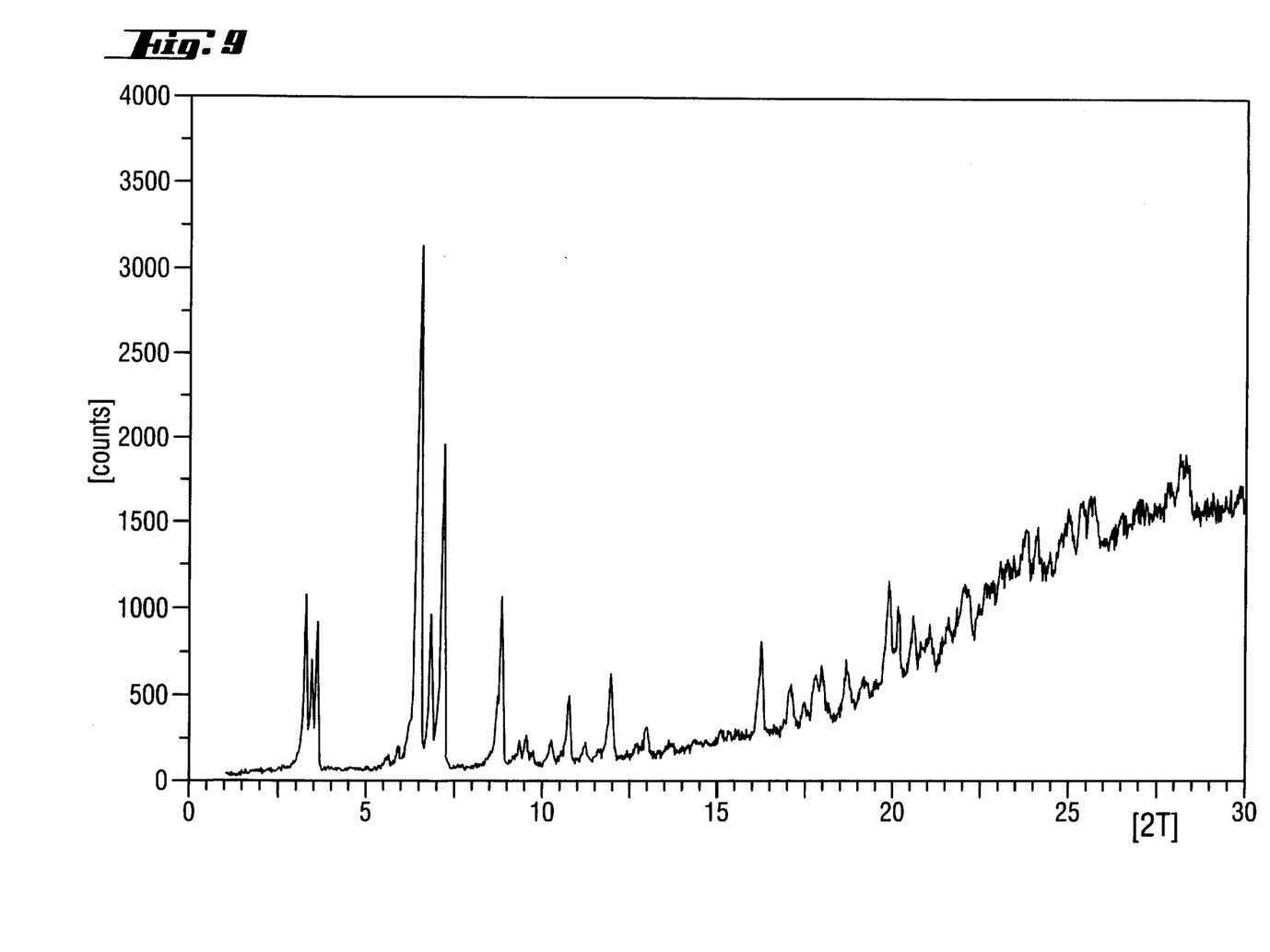
Figure 10:
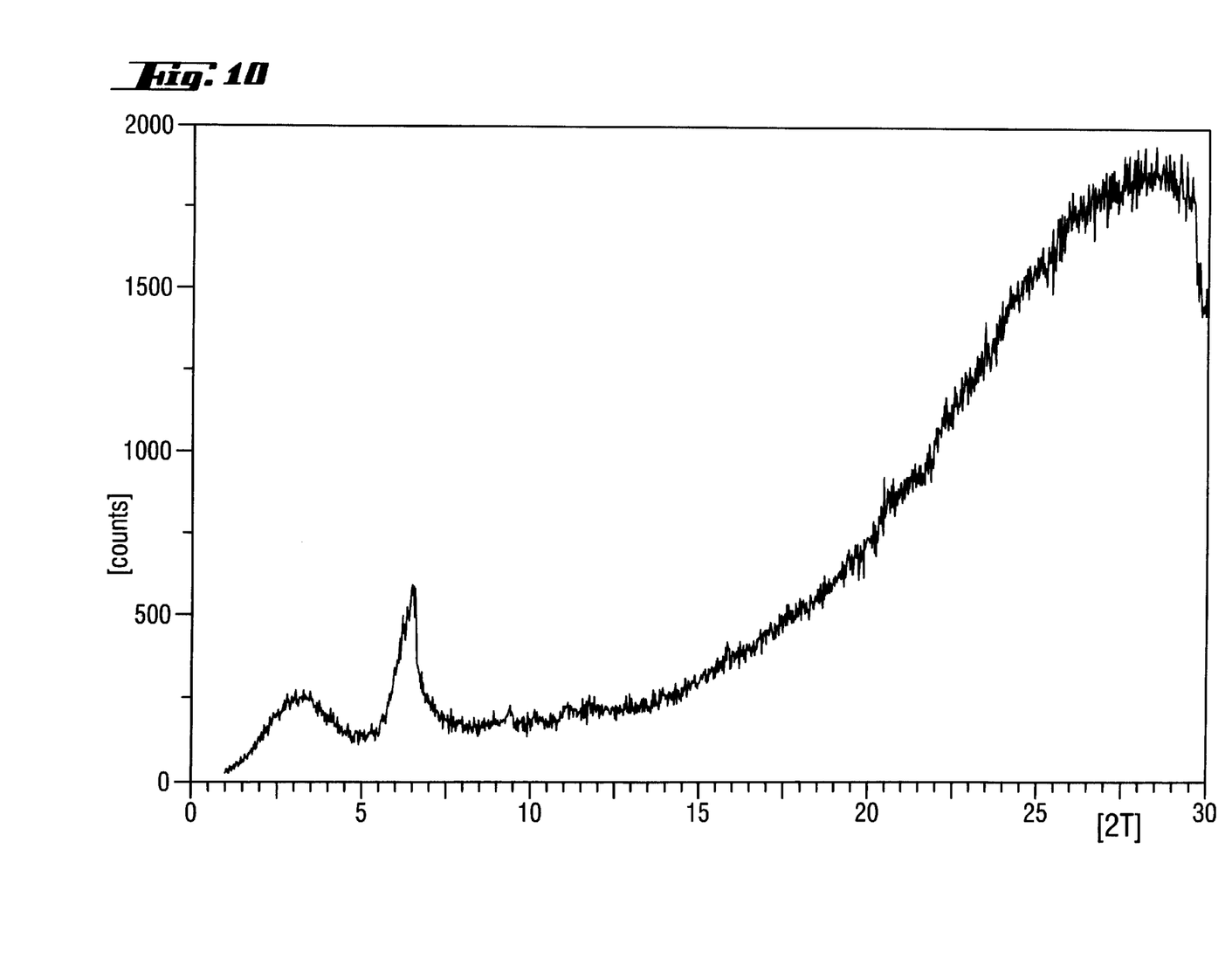
Figure 11:
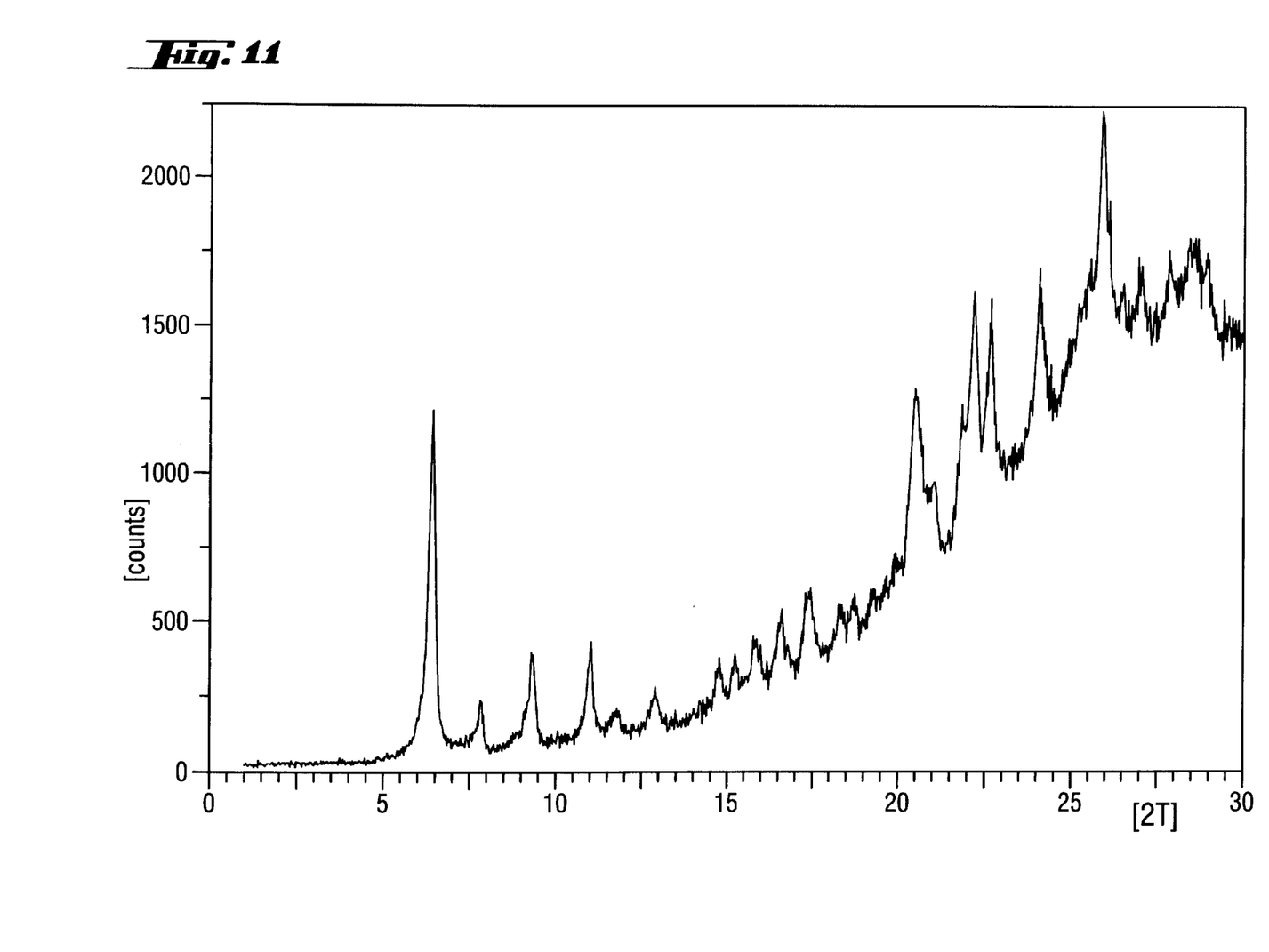

Further preferred hydrates of the 4,4'-di-triazinylamino-2,2'-di-sulfostilbene compound (I) are those in which M and $M_1$ both represent potassium, the hydrate being characterised by an X-ray diffraction pattern which is essentially as set out in the accompanying FIG. 8 and in which x represents 9 to 17 and those in which M and $M_1$ both represent lithium, the hydrates being characterised by an X-ray diffraction pattern which is essentially as set out in the accompanying FIGS. 9 to 11; or a mixture containing one or more of the hydrates of the 4,4'-di-triazinylamino-2,2'-di-sulfostilbene compound having the formula (I), M and $M_1$ representing lithium and in which x represents 9 to 30.

Further hydrates of interest are such hydrates of the 4,4'-di-triazinylamino-2,2'-di-sulfostilbene compound (I) in which M and $M_1$ both represent calcium or magnesium and also those in which M and $M_1$ both represent ammonium.

In compounds of formula (I) in which M and $M_1$ both represent ammonium these may be represented by the formula $-N(R)_4$, whereby R represents hydrogen or $C_1$–$C_4$-alkyl, all R-groups not necessarily being identical, or $C_2$–$C_4$-alkanolammonium.

The respective X-ray diffraction patterns, FIGS. 1 to 11, are obtained using an X'Pert powder diffractometer (Philips, Almelo) in reflexion geometry and Cu radiation. The reference patterns for crystal forms B (FIG. 1) and C (FIG. 2) are measured in suspensions in an atmosphere of air, without control of relative humidity. The measurement of the reference patterns for crystal form D (FIG. 3), E (FIG. 4), F (FIG. 6) and G (FIG. 7) and also that of the di-potassium salt (FIG. 8) are also conducted in suspensions, under nitrogen, while maintaining the relative humidity at a level of 80–90%, as are those of the three crystal forms of the di-lithium salt (FIGS. 9–11), whilst that of crystal form A (FIG. 5) was conducted in the solid state. In each of the accompanying FIGS. 1 to 11, there is shown the part of the measurements in the 2θ-area between 1° and 30°.

Each of the novel hydrates of formula (I) has a characteristic X-ray diffraction pattern.

The crystal forms A, B, C, D, E, F and G and also those of the di-potassium and lithium salts consist for the most part of one or more hydrates of the formula (I) in which x is a number between 1 and 30.

The amount of water of hydration may be determined via differential thermal analysis or dynamic differential calorimetry in which the proportion of the unbound water, that is the water melting at 0° C., is measured, or by subsequent water analysis by methods such as Karl Fischer titration, thermogravimetric analysis or loss on drying at elevated temperature.

The di-sodium salt of 4,4'-di-triazinylamino-2,2'-di-sulfostilbene possessing the (A) hydrate form may be produced by successively reacting cyanuric chloride with 4,4'-diaminostilbene disulphonic acid di-sodium salt, aniline and diethanolamine, adjusting the pH of the mixture to 9.0 to 9.5 with concentrated sodium hydroxide solution and evaporating the mixture to dryness. If, prior to treatment with sodium hydroxide, the compound is isolated in the form of the free acid, a hydrate results possessing the (F) crystal form.

The (C) hydrate crystal form may be obtained by neutralization of the free acid of 4,4'-di-triazinylamino-2,2'-disulfostilbene possessing the (A) hydrate form with dilute sodium hydroxide solution, homogenising and allowing to stand at room temperature; the (D) hydrate crystal form by treatment of the sodium salt of 4,4'-di-triazinylamino-2,2'-di-sulfostilbene possessing the (A) hydrate form aqueous sodium chloride solution, stabilizing and homogenising; and the (E) hydrate crystal form by treatment of the free acid of 4,4'-di-triazinylamino-2,2'-di-sulfostilbene possessing the (A) hydrate form with concentrated sodium hydroxide solution and homogenising. The (G) crystal form of the hydrate may be obtained from the (E) form by equilibration in a closed vessel at elevated temperature.

The (C) hydrate can further be prepared by seeding an aqueous suspension of the corresponding free acid, with (C) seed crystals. This technique has the advantage that active substance concentrations of more than 30% by weight, preferably 30 to 50% by weight, can be used and thus the suspension obtained is formed in the desired concentration and does not have to be concentrated.

Figure 3:
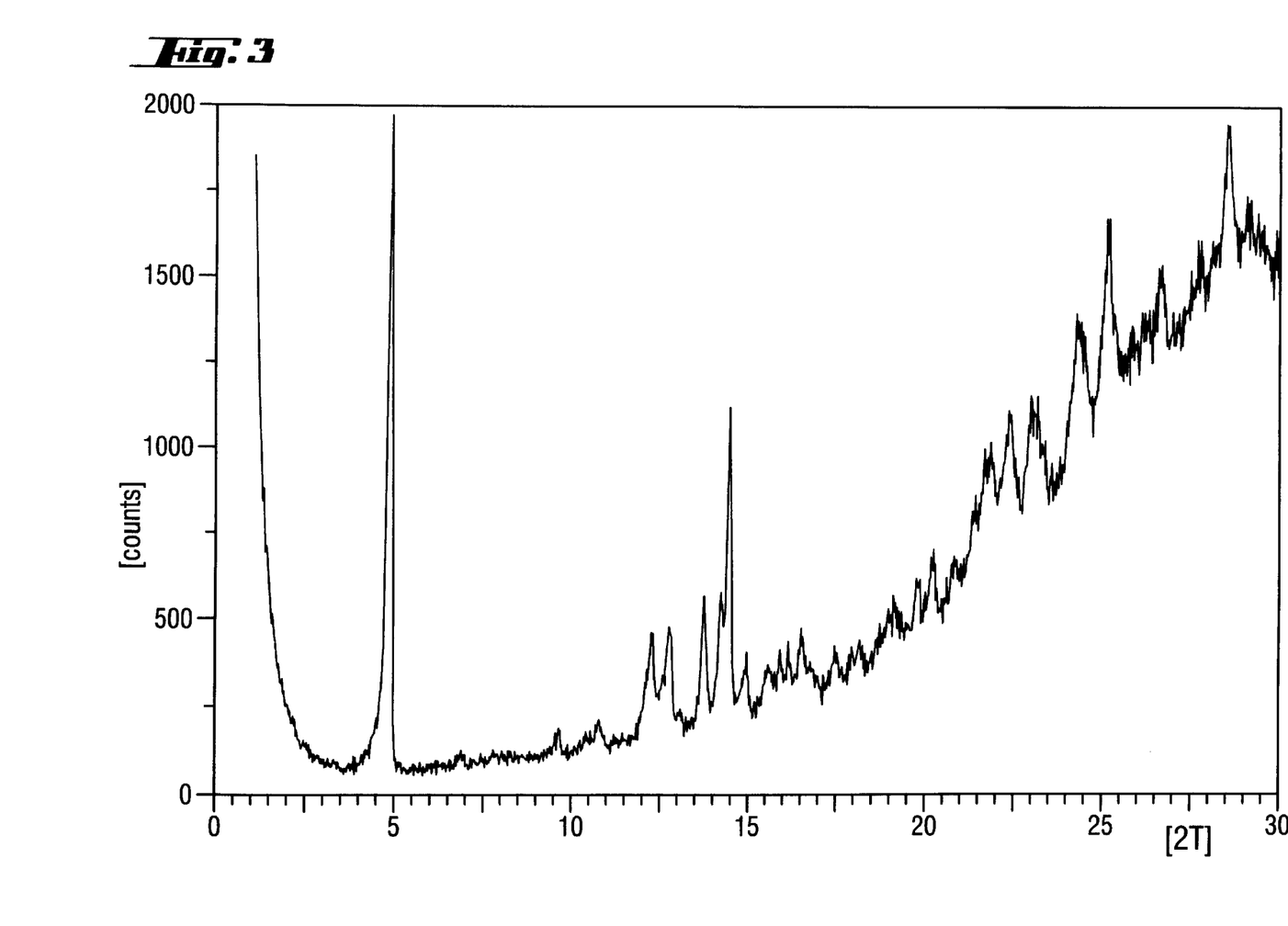
Figure 4:
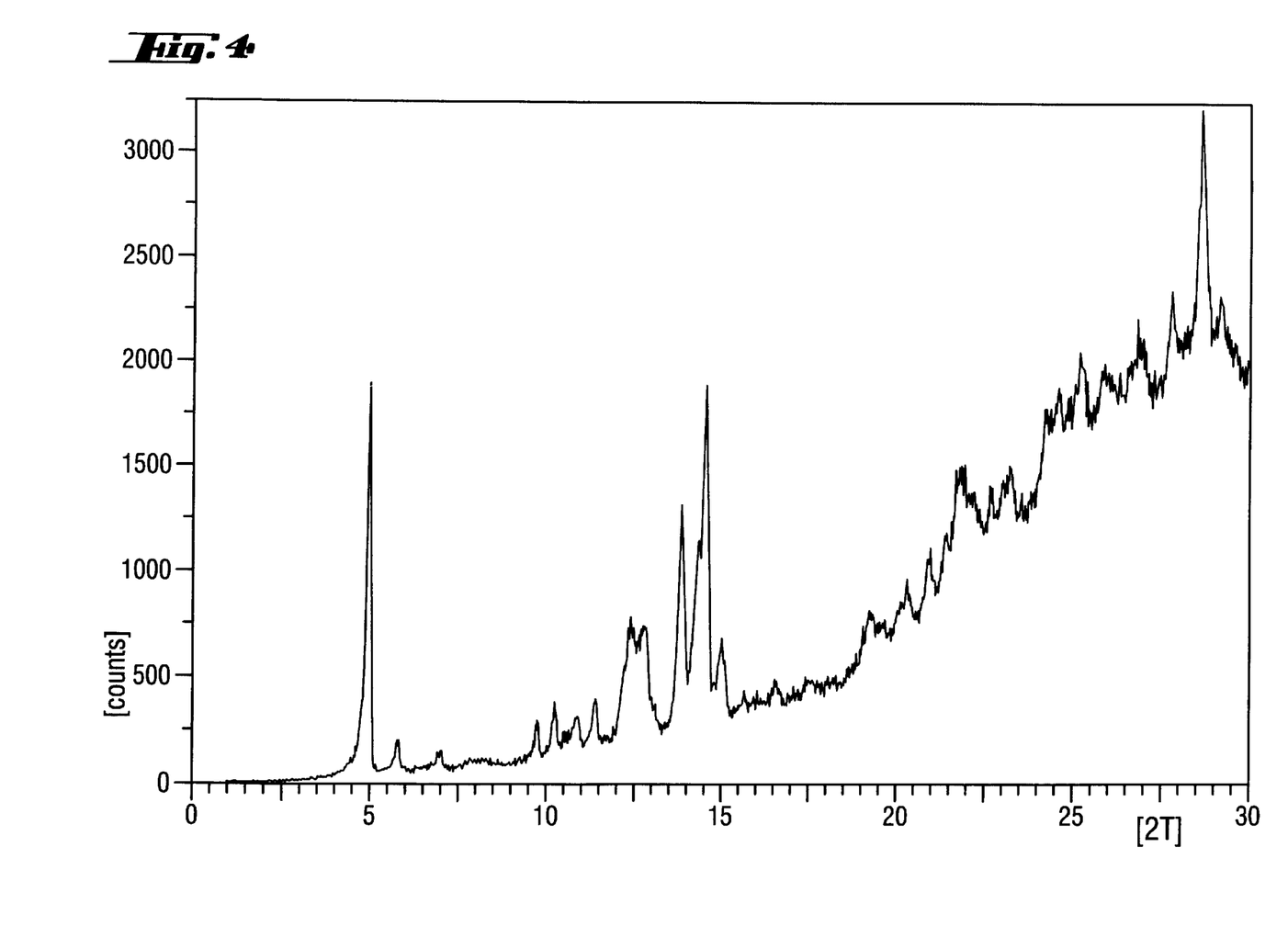
Figure 5:
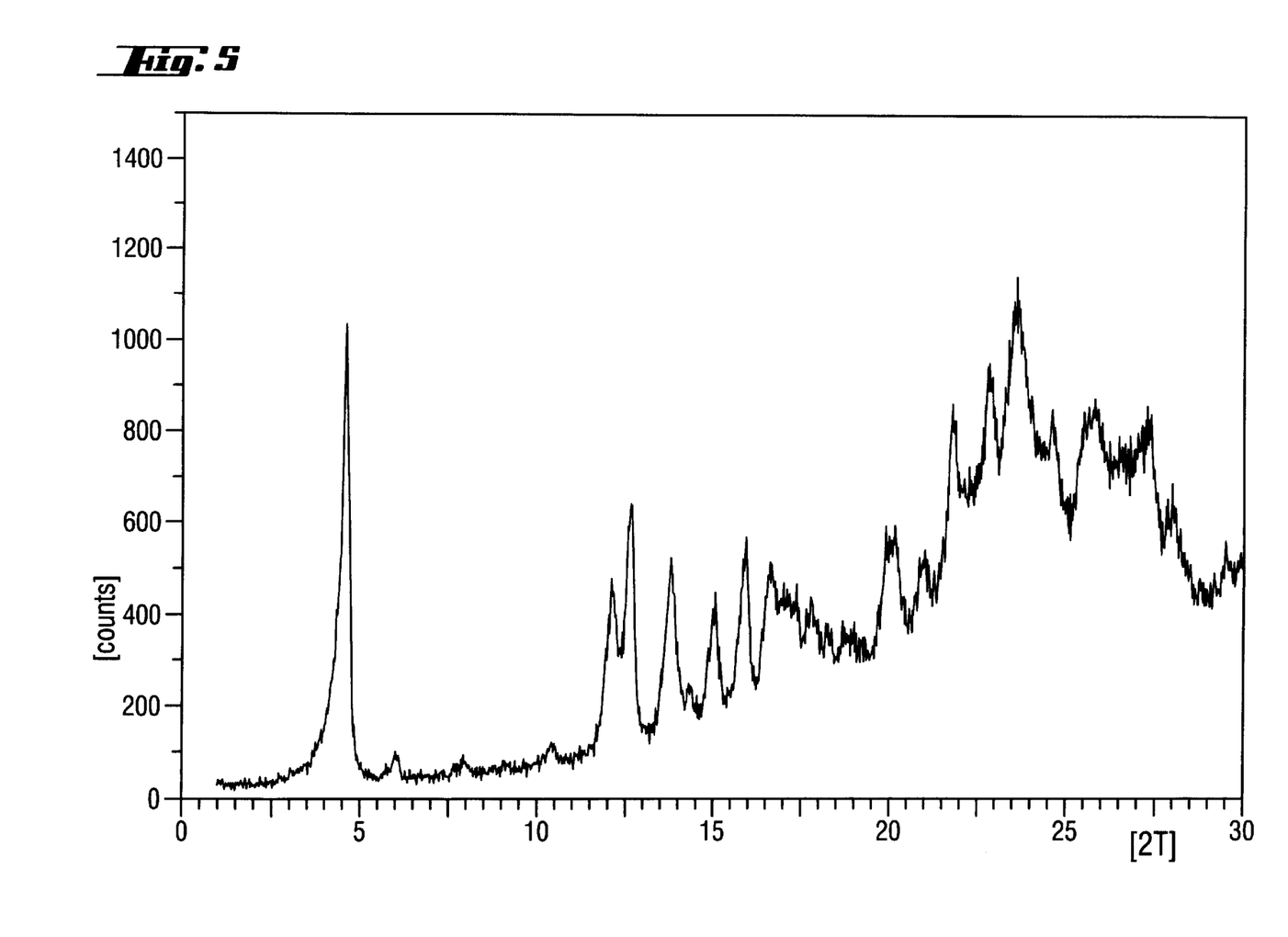
Figure 6:
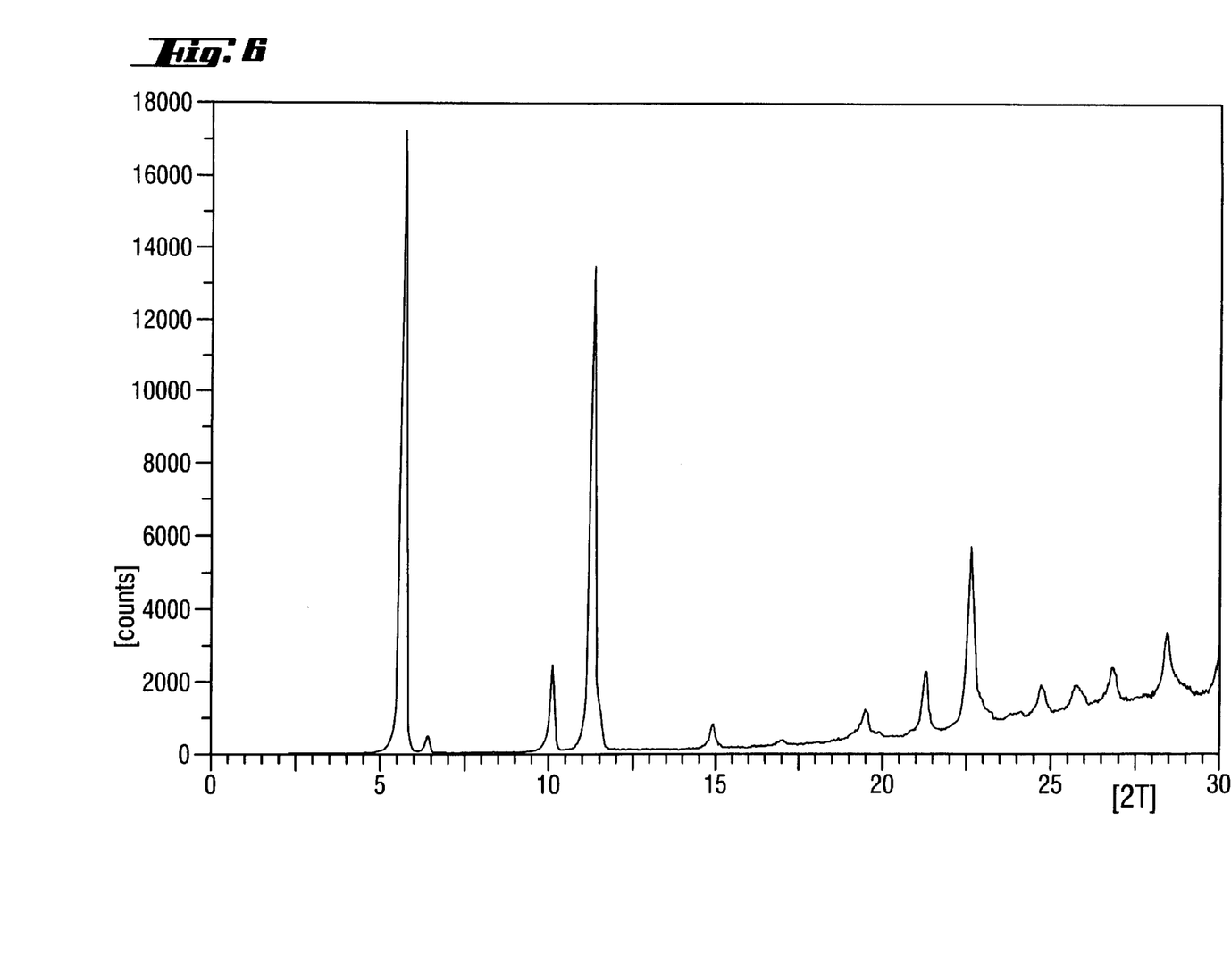
Figure 7:
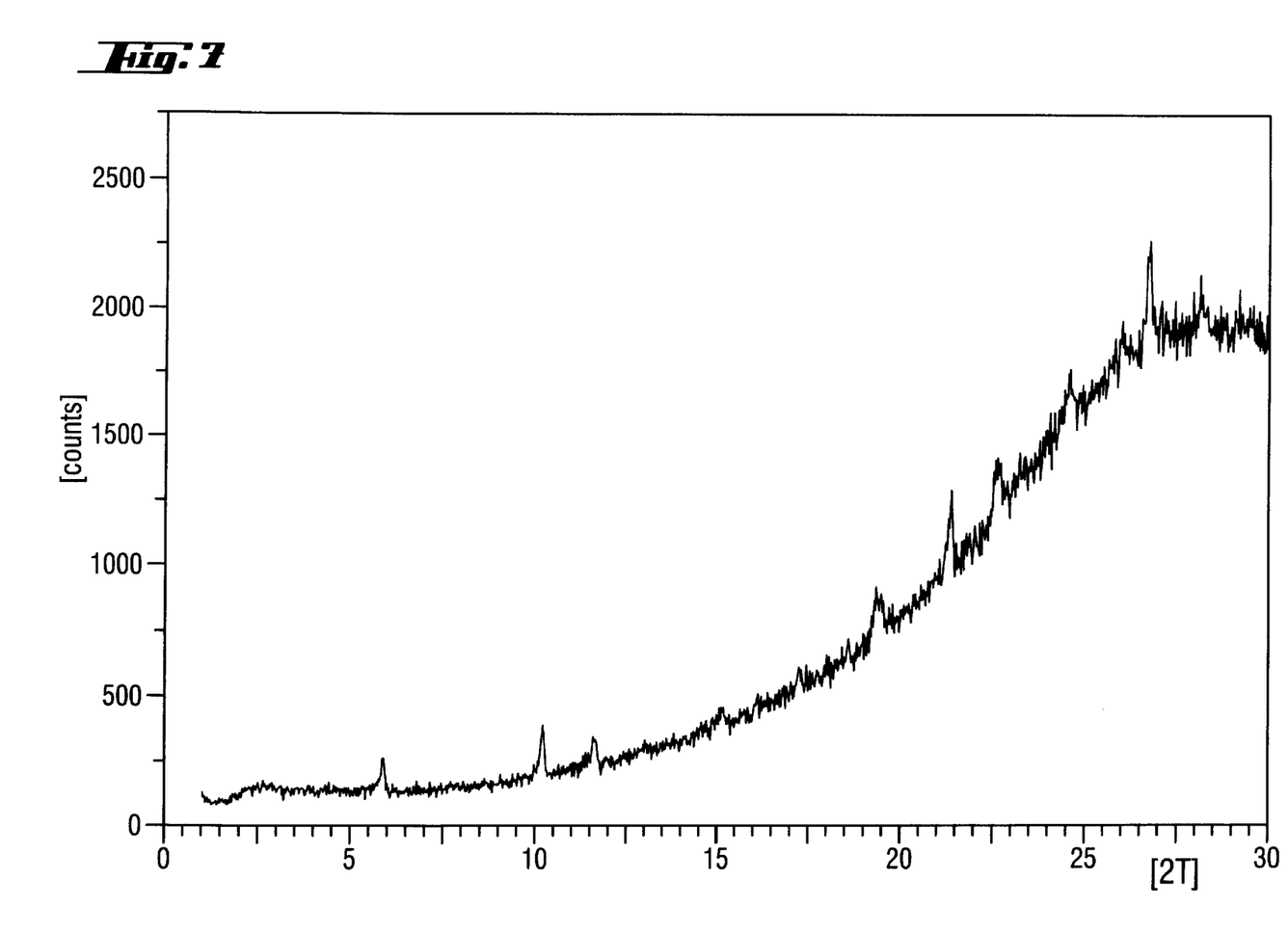

The hydrate of crystal form (D) in accordance with FIG. 3, or the hydrate of crystal form which is designated as (E) form and characterised by an X-ray diffraction pattern which is essentially as in FIG. 4, may also be prepared by the seeding technique described in relation to the production of the (C) form.

In a preferred embodiment, a mixture of one or more of the novel hydrates of formula (I) is prepared by the controlled mixing of an aqueous solution of an inorganic salt electrolyte, preferably an alkali metal halide or sulfate, especially sodium chloride or sodium sulfate; and the active substance of formula (I). The process is conveniently conducted by firstly preparing an aqueous solution of the electrolyte and then seeding this electrolyte solution with a previously-prepared sample of the active substance of formula (I). While maintaining the pH value of the seeded electrolyte solution within the range of from 7.5 to 9.0, preferably from 8.0 to 8.5, active substance of formula (I), as the free acid, alkali, preferably sodium hydroxide and water are preferably added, simultaneously and portionwise, to the seeded electrolyte solution. Preferably, water and the free acid form of the active substance are added until a) the content of the active substance in the synthesis mixture is within the range of from 5 to 40%, preferably from 10 to 30% and especially from 15 to 25% by weight and b) the content of electrolyte in the synthesis mixture is within the range of from 0.5 to 2.5%, preferably from 1 to 2% and especially about 1.5% by weight.

The seed crystals should be used in the form of small crystals whose average size does not markedly exceed 10 micron. This allows the substantial reduction of the seed crystal content, for example down to 0.1 to 5% by weight, relative to the total active substance content. The seeding is preferably effected without stirring.

The seed crystal content is in general between 0.1 and 60% by weight, preferably between 1 and 50% by weight, and particularly preferably between 1 and 30% by weight, relative to the total active substance content. In all cases in which only a portion of the final compound is replaced by new starting material, the conversion can be carried out as semi-continuous or continuous process.

The reaction temperature for preparing the mixtures of hydrate of formula (I) according to the present invention preferably lies within the range of from 10–95° C. and preferably within the range of from 35–55° C.

The di-potassium and lithium salts of 4,4'-di-triazinylamino-2,2'-di-sulfostilbene (I) may be obtained by neutralising the free acid form of 4,4'-di-triazinylamino-2, 2'-di-sulfostilbene with potassium or lithium hydroxide, respectively. In the case of the di-lithium salt, two further crystal forms of the hydrates may be obtained by equilibrating a slurry of the salt obtained directly by neutralisation at elevated temperatures.

The invention also provides an aqueous formulation containing 30–50% by weight of active substance in the form of one or more of novel hydrate forms of the formula (I). This formulation remains flowable, has good metering characteristics, and is stable for months, without forming sediments, even after standing at temperatures of between 5–40° C. for an extended period of time.

An aqueous formulation containing 30–50% by weight of active substance in the form of one or more of novel hydrate forms A, B, C, D, E, F and G of the formula (I) is highly viscous when no formulation auxiliaries are added and is suitable for the production of brushable pastes or for being incorporated therein.

Thus, by incorporating the active substance in the form of one or more of novel hydrate forms of the formula (I) having different crystal forms, a desired viscosity of an aqueous formulation can be selectively established, without the presence of any further auxiliaries. An electrolyte, for example NaCl or $Na_2SO_4$, or a mixture thereof, can be admixed with the aqueous formulation in order to stabilise the hydrates contained therein.

A particular advantage of the hydrates according to the present invention having different crystal forms is that they enable ready-to-use and stable formulations of a wide range of viscosities to be produced, without addition of ecologically harmful formulation auxiliaries.

If desired, however, the formulations obtained according to the present invention may contain customary formulation auxiliaries, such as dispersing agents, builders, protective colloids, stabilisers, preservatives, perfumes and sequestering agents.

Dispersing agents are preferably anionic dispersing agents, such as condensation products of aromatic sulfonic acids with formaldehyde, for example ditolylethersulfonic acid, a naphthalenesulfonate or a ligninsulfonate.

Examples of suitable builders or protective colloids are modified polysaccharides derived from cellulose or heteropolysaccharides, such as xanthan, carboxymethylcellulose and polyvinyl alcohols (PVA), polyvinylpyrrolidones (PVP), polyethylene glycols (PEG) and aluminium silicates or magnesium silicates. They are usually used in a concentration range of 0.01 to 2% by weight and preferably 0.05 to 0.5% by weight, relative to the total weight of the formulation.

Examples of auxiliaries which can be used for stabilisation are ethylene glycol, propylene glycol or dispersants in an amount of 0.2 to 5% by weight and preferably 0.3 to 2% by eight, relative to the total weight of the formulation. Compounds which may be used as stabilisers include 1,2-benzisothiazolin-3-one, formaldehyde or chloroacetamide in an amount of 0.1 to 1% by weight and preferably 0.1 to 0.5% by weight relative to the total weight of the formulation.

The concentrated formulation thus prepared can be used for the fluorescent whitening of paper or textile material, for example in detergents. To this end, they are in general diluted to the optimum concentration for the practical application by the addition of further auxiliaries or water.

The following Examples further illustrate the present invention. Parts and percentages shown therein are by weight unless otherwise stated.

EXAMPLE 1

In a reaction vessel, 400 g of ice, 120 g of cyanuric chloride and 785 g of methyl ethyl ketone are mixed and, with intensive stirring and external cooling, treated with a solution of 120 g of 4,4'-diaminostilbene-2,2'-disulphonic acid disodium salt in 800 g of water and 164.5 g of 17% sodium carbonate solution over 20 minutes at 5–10° C., the pH being maintained at 4.5 by the simultaneous addition of 39.4 g of 17% sodium carbonate solution. After the addition, 55.4 g of aniline and 8.7 g of diethanolamine are added, the pH being maintained at 7.5 by the simultaneous addition of 72.2 g of 36% sodium hydroxide solution. After heating to 60° C, 78.8 g of diethanolamine are added whilst maintaining the pH at 8.2 by the simultaneous addition of 72.2 g of 36% sodium hydroxide solution. The reaction mixture is heated to reflux and the methyl ethyl ketone destined off, being gradually replaced by 1000 g of water. At a temperature of 95° C., the mixture is acidified to pH 4.5 by the addition of 170 g of 16% hydrochloric acid solution and the volume adjusted to 2.71 by addition of water. After cooling to 70° C., the mixture is filtered and the filter cake washed with 1.81 of water to yield the free acid. A 30% aqueous suspension of this free acid is heated to 95° C. and the pH adjusted to 9.0–9.5 by the addition of 36% sodium hydroxide solution. The resulting solution is then evaporated to dryness to yield a compound of Formula (1) as the di-sodium salt, which has the A-crystal form containing 1 mole of water, corresponding to the X-ray diffraction pattern which is set out in the accompanying FIG. 5.

EXAMPLE 2

75.0g of the free acid form (having an active substance content of 40% by weight) of the di-sodium salt of formula (I) are dispersed in 24.7 g of deionised water at 25° C. The dispersion so obtained is stabilised by adding to it 0.2 g of xanthan gum and 0.1 g of Proxel GXL (1,2-benzisothiazolin-3-one) and the mixture is homogenised. The homogenised suspension is neutralised with 32.8 mls of a 2N aqueous sodium hydroxide solution. The homogenised, neutralised suspension has the B-crystal form which corresponds to the X-ray diffraction pattern which is set out in the accompanying FIG. 1.

Figure 1:
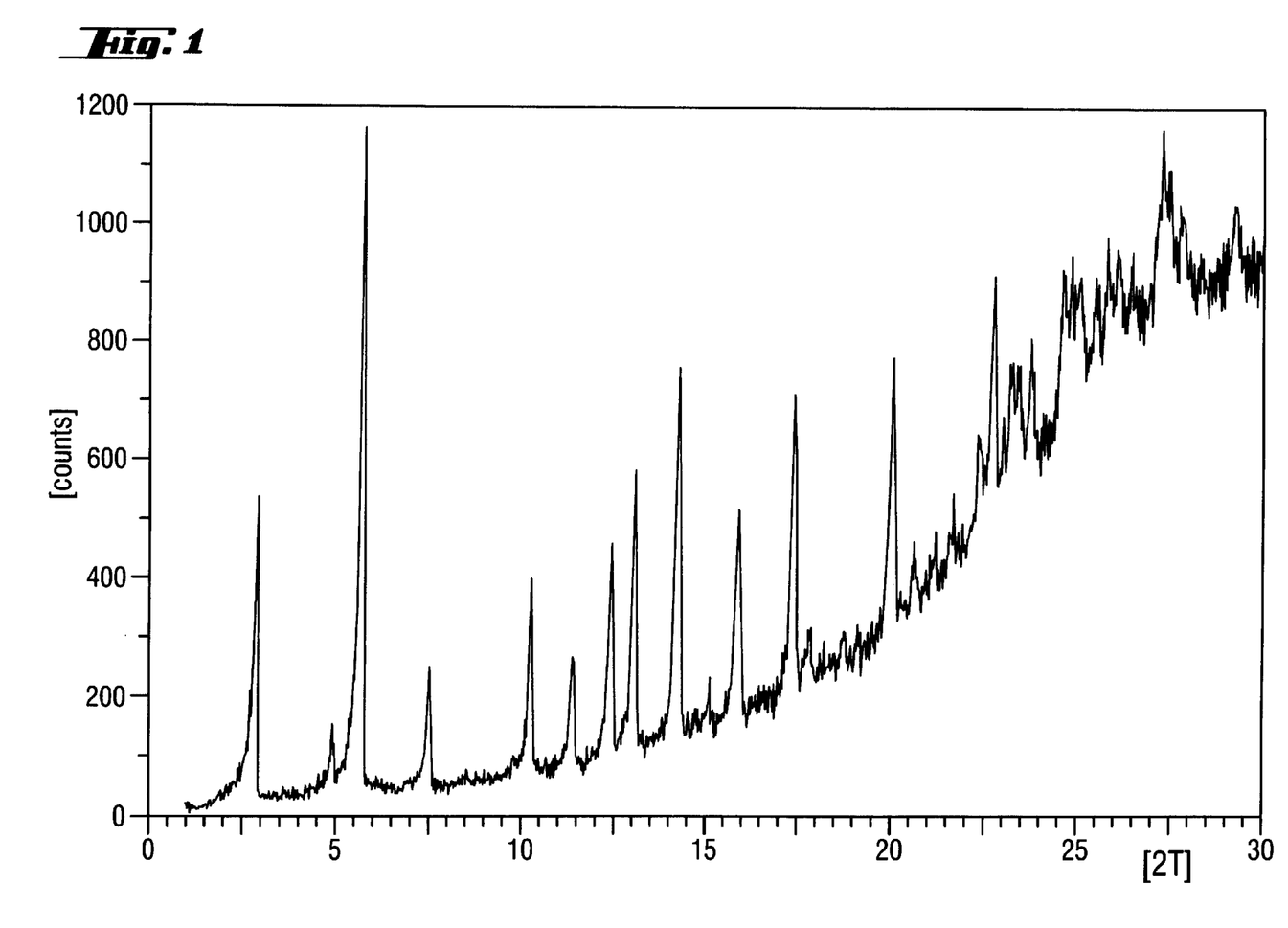
Figure 2:
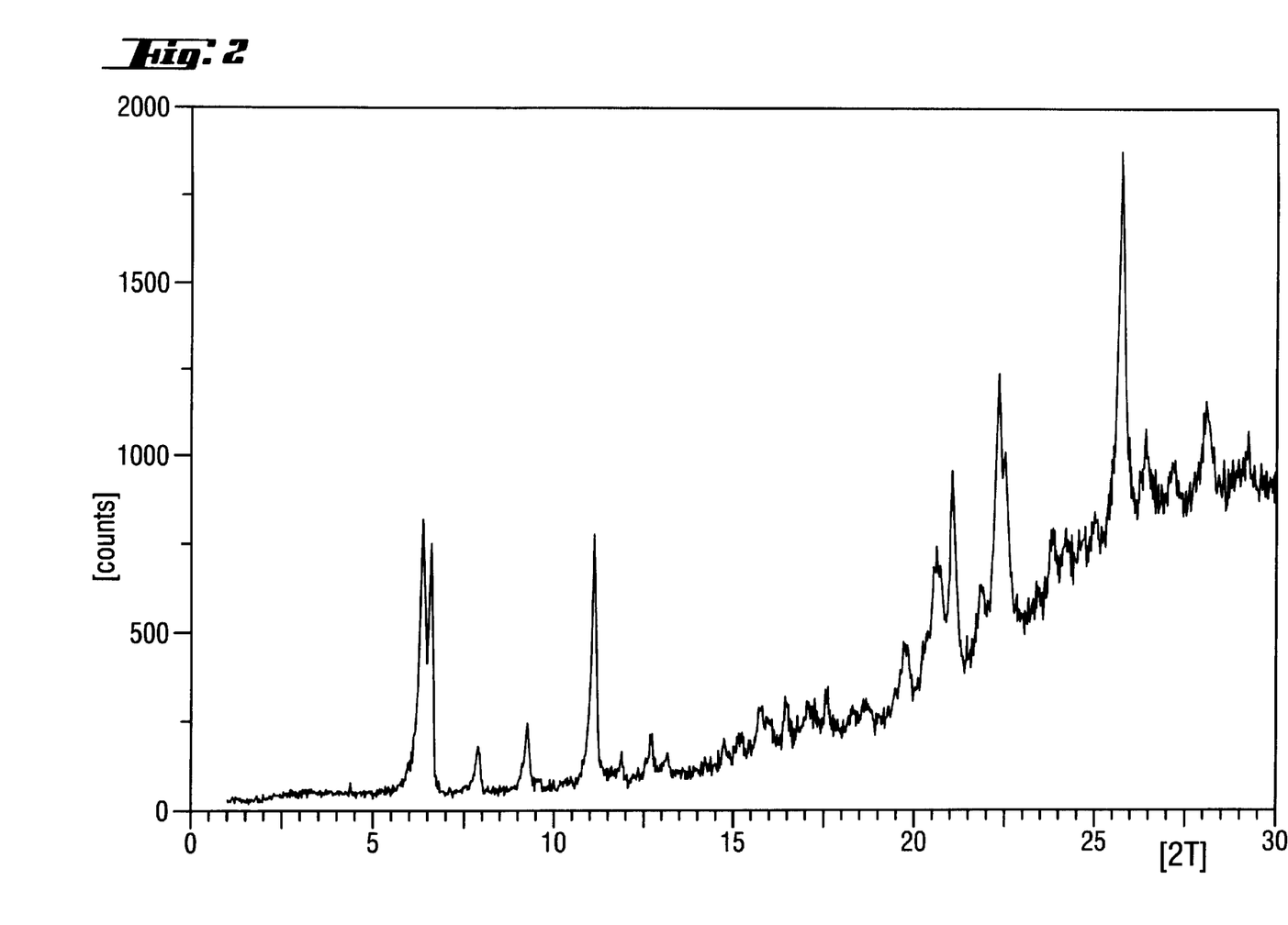

After standing for two days at 25° C., a suspension is obtained which is readily pourable and which has the C-crystal form containing 17 moles of water which corresponds to the X-ray diffraction pattern which is set out in the accompanying FIG. 2.

Using the same procedure, but using, as starting material, the di-sodium salt of formula (I) in the form of a pure hydrate of the A, B, D, E, F or G crystal form, or a mixture thereof, a suspension is obtained which is readily pourable and which has the C-crystal form containing 17 moles of water, which corresponds to the X-ray diffraction pattern which is set out in the accompanying FIG. 2.

EXAMPLE 3

700 g of the moist filter cake from Example 1 (≡265 g of free acid) are gradually added to 314 g of water at 40–45° C. whilst maintaining the pH at 8.7–9.1 by the simultaneous addition of 64 g of 36% sodium hydroxide solution. Then, at 42° C., 20 g of seed crystals of the C form of the hydrate obtained in Example 2 are added. After 5 hours, the liquid dispersion is cooled to 25–30° C. and stabilised by the addition of 2.2 g of 50% glutaraldehyde solution and 2.2 g of xanthan gum (polysaccharide), predispersed in 5.5 g of propylene glycol. A liquid suspension is obtained which is readily pourable and which has the C-crystal form containing 17 moles of water, which corresponds to the X-ray diffraction pattern which is set out in the accompanying FIG. 2.

EXAMPLE 4

In a reaction flask, 400 g of a 6% aqueous sodium chloride solution are pre-heated to 60° C. Into this solution are introduced 120 g of the di-sodium salt of formula (I) (having an active substance content of 90% by weight and containing 10% sodium chloride) and the mixture is heated to 90° C. 180 g of 6% aqueous sodium chloride solution are added and the mixture is cooled, with stirring, to 25° C. The resulting liquid suspension is stabilised by the addition of 2.45 g of xanthan gum which has been pre-dispersed in 6.1 g of 1,2-propylene glycol and the mixture is heated to 90° C. for two hours. The mixture is cooled, with stirring, to 25° C., 3.22 g of Proxel GXL (1,2-benzisothiazolin-3-one) are added, as stabiliser, the mixture is stirred for a further twelve hours and finally homogenised using a high speed stirrer. A suspension is obtained which has the D-crystal form containing 14 moles of water, which corresponds to the X-ray diffraction pattern which is set out in the accompanying FIG. 3.

EXAMPLE 5

In a reaction flask, 400 mls of deionised water are pre-heated to 40° C. Into this water are introduced, portionwise, 800 g of the free acid form (having an active substance content of 40% by weight) of the di-sodium salt of formula (I) and, by the simultaneous portionwise addition of 50.45 mls of a 37% (50% g/v %) aqueous sodium hydroxide solution, the pH value of the mixture is kept constant at 8.2. After the addition is complete, the whole is diluted with 400 mls of deionised water, stirred for one hour and then homogenised. A suspension is obtained which has the E-crystal form containing 14 moles of water, which corresponds to the X-ray diffraction pattern which is set out in the accompanying FIG. 4.

EXAMPLE 6

620 g of the moist filter cake obtained as in Example 1 (≡279 g free acid) are dispersed in 304 g of water and stabilised by the addition of 1.7 g of Proxel GXL and 1.7 g of xanthan gum (polysaccharide), predispersed in 3.3 g of propylene glycol. A liquid suspension is obtained which has the F crystal form containing 7 moles of water, which corresponds to the X-ray diffraction pattern which is set out in the accompanying FIG. 6.

EXAMPLE 7

A 20% slurry of the E crystal form of the hydrate, obtained as in Example 5, is stirred in a closed vessel at 60° C. and maintained at this temperature for at least 20 hours. After cooling to room temperature, a liquid suspension is obtained which has the G crystal form containing 7 moles of water, which corresponds to the X-ray diffraction pattern which is set out in the accompanying FIG. 7.

EXAMPLE 8

400 mls of a 6.0% by weight aqueous sodium chloride solution are prepared. This solution is then seeded with a previously-prepared batch of an aqueous slurry of the di-sodium salt of formula (II). The temperature of the seeded solution is adjusted to 45° C., and there are simultaneously added to the seeded solution, a) a moist aqueous presscake of the free acid form (active substance content 40% by weight) of the di-sodium salt of formula (II), b) aqueous sodium hydroxide solution and c) water, while maintaining the pH value of the resulting mixture constant at 8.2. Water and the moist aqueous presscake of the free acid form are added until the content of active substance of the free acid form in the reaction mixture is within the range of from 15 to 25% by weight and the content of sodium chloride in the reaction mixture is 1.5% by weight.

The aqueous formulation so obtained is examined using an X'Pert powder diffractometer (Philips, Almelo) in reflexion geometry and Cu radiation. The device is fitted with a closed sample chamber (Anton Parr) which can be adapted to be purged with gas. The aqueous formulation is filled tel quel into the sample carrier (layer thickness 0.8 mm) and the measurement of the powder diagram is conducted under nitrogen, while maintaining the relative humidity at a level of 80–90%. The aqueous formulation so obtained is found to consist of pure hydrates of crystal form A, B, C, D, E, F or G or mixtures thereof.

EXAMPLE 9

Similar results are obtained when an aqueous solution of sodium sulfate is used as starting material in Example 8 instead of the aqueous solution of sodium chloride.

EXAMPLE 10

400 mis of a 3.0% by weight aqueous sodium chloride solution are prepared. This solution is then seeded with a previously-prepared batch of an aqueous slurry of the di-sodium salt of formula (II). The temperature of the seeded solution is adjusted to 45° C., and there are simultaneously added to the seeded solution, a) a moist aqueous presscake of the free acid form (active substance content 40% by weight) of the di-sodium salt of formula (II), b) aqueous sodium hydroxide solution and c) water, while maintaining the pH value of the resulting mixture constant at 8.2. Water and the moist aqueous presscake of the free acid form are added until the content of active substance of the free acid form in the reaction mixture is within the range of from 15 to 25% by weight and the content of sodium chloride in the reaction mixture is 0.75% by weight.

The aqueous formulation so obtained is examined using an X'Pert powder diffractometer (Philips, Almelo) in reflexion geometry and Cu radiation. The aqueous formulation so obtained is found to be a pure hydrate of crystal form A, B, C, D, E, F or G or mixtures thereof.

EXAMPLE 11

Similar results are obtained when an aqueous solution of sodium sulfate is used as starting material in Example 10 instead of the aqueous solution of sodium chloride.

EXAMPLE 12

400 mis of a 1.5% by weight aqueous sodium chloride solution are prepared. This solution is then seeded with a previously-prepared batch of an aqueous slurry of the di-sodium salt of formula (I). The temperature of the seeded solution is adjusted to 45° C., and there are simultaneously added to the seeded solution, a) a moist aqueous presscake of the free acid form (active substance content 40% by weight) of the di-sodium salt of formula (I), b) aqueous sodium hydroxide solution and c) water, while maintaining the pH value of the resulting mixture constant at 8.2. Water and the moist aqueous presscake of the free acid form are added until the content of active substance of the free acid form in the reaction mixture is within the range of from 15 to 25% by weight and the content of sodium chloride in the reaction mixture is 0.25% by weight.

The aqueous formulation so obtained is examined using an X'Pert powder diffractometer (Philips, Almelo) in reflexion geometry and Cu radiation. The aqueous formulation so obtained is found to be a pure hydrate of crystal form A, B. C, D, E, F or G or mixtures thereof.

EXAMPLE 13

Similar results are obtained when an aqueous solution of sodium sulfate is used as starting material in Example 12 instead of the aqueous solution of sodium chloride.

EXAMPLE 14

400 mis of a 1.5% by weight aqueous sodium chloride solution are prepared. This solution is then seeded with a previously-prepared batch of an aqueous slurry of the di-sodium salt of formula (I). The temperature of the seeded solution is adjusted to 45° C., and there are simultaneously added to the seeded solution a) a moist aqueous presscake the di-sodium salt of formula (I) (active substance content 40% by weight), b) aqueous sodium hydroxide solution and c) water, while maintaining the pH value of the resulting mixture constant at 8.2. Water and the moist aqueous presscake of the free acid form are added until the content of active substance of the free acid form in the reaction mixture is within the range of from 15 to 25% by weight and the content of sodium chloride in the reaction mixture is 0.25% by weight.

The aqueous formulation so obtained is examined using an X'Pert powder diffractometer (Philips, Almelo) in reflexion geometry and Cu radiation. The aqueous formulation so obtained is found to be a pure hydrate of crystal form A, B, C, D, E, F or G or mixtures thereof.

EXAMPLE 15

400 mis of a 1.5% by weight aqueous sodium chloride solution are prepared. This solution is then seeded with a previously-prepared batch of the di-sodium salt of formula (I). The previously-prepared batch of the di-sodium salt of formula (I) is prepared in an organic phase, containing the free acid form of the active substance, and is obtained in the last reaction step which is conducted at 90–100° C. The temperature of the seeded solution is adjusted to 45° C., and there are simultaneously added to the seeded solution a) the said organic phase containing the free acid form of the active substance and b) water. Water and the said organic phase containing the free acid form of the active substance are added until the content of active substance of the free acid form in the reaction mixture is within the range of from 15 to 25% by weight and the content of sodium chloride in the reaction mixture is 0.25% by weight.

The aqueous formulation so obtained is examined using an X'Pert powder diffractometer (Philips, Almelo) in reflexion geometry and Cu radiation. The aqueous formulation so obtained is found to be a pure hydrate of crystal form A, B, C, D, E, F or G or mixtures thereof.

EXAMPLE 16

Similar results are obtained when an aqueous solution of sodium sulfate is used as starting material in Example 15 instead of the aqueous solution of sodium chloride.

EXAMPLE 17

75.0 g of the free acid of 4,4'-di-triazinylamino-2,2'-di-sulfostilbene possessing the (A) hydrate form (active content 40%) are dispersed in 24.7 g of deionised water, 0.2 g polysaccharide (xanthan gum type) and 0.1 g of Proxel GXL added and the mixture homogenised. After storing for 24 hours at 40° C. or at 60° C., the mixture is neutralised with 32.8ml of 2N potassium hydroxide solution. After storing at room temperature, a readily pourable suspension of the di-potassium salt is obtained which contains 13 moles of water, characterised by an X-ray diffraction pattern which is shown in FIG. 8.

EXAMPLE 18

75.0 g of the free acid of 4,4'-di-triazinylamino-2,2'-di-sulfostilbene possessing the (A) hydrate form (active content 40%) are dispersed in 24.7 g of deionised water, 0.2 g polysaccharide (xanthan gum) and 0.1 g of Proxel GXL added and the mixture homogenised. After storing for 24 hours at 40° C., the mixture is neutralised with 32.8 ml of 2N lithium hydroxide solution. After storing at room temperature, a readily pourable suspension of the di-lithium salt is obtained which contains 29 moles of water, characterised by an X-ray diffraction pattern which is shown in FIG. 9.

EXAMPLE 19

10 g of the di-lithium salt obtained as in Example 18 are stirred in a closed vessel at 60° C. After 15 minutes a clear solution results which, after prolonged stirring, then begins to reprecipitate. After stirring for 12 hours at the same temperature, the mixture is cooled and the precipitated solid filtered off. A di-lithium salt is obtained which contains 14 moles of water, characterised by an X-ray diffraction pattern which is shown in FIG. 10.

EXAMPLE 20

Example 19 is repeated but carrying out the equilibration at a temperature of 55° C. A di-lithium salt is obtained which contains 13 moles of water, characterised by an X-ray diffraction pattern which is shown in FIG. 11.

EXAMPLE 21

A pulp suspension of sulfite beech/spruce (50:50) is stirred in water (containing 25 ppm CaO) in the presence of 20% by weight of calcium carbonate, as filler.

0.4% by weight of each of the products of Examples 1 to 20 are added to a separate sample of the pulp suspension, and each test slurry is stirred for 15 minutes. A paper sheet is formed from each of the test pulp suspensions with an area weight of 80 g/m², and the respective paper sheets are dried. The whiteness (CIE-Whiteness measured by SCAN-P 66:93) of each dried sheet is determined and found to be from 140–142. The CIE whiteness of paper produced in the same way but in the absence of a fluorescent whitening agent formulation according to the present invention is only 75.

What is claimed is:

1. A process for the production of the di-sodium salt of the 4,4'-di-triazinylamino-2,2'-di-sulfostilbene compound having the formula:

in which M and $M_1$ are sodium and x represents 1 to 6 and possessing the (A) hydrate form characterized by an X-ray diffraction pattern which shows absorptions in the 2Ø-area between 1° and 30° as follows:
4.6 (very strong), 6.1 (very weak), 8.0 (very weak), 10.5 (very weak), 12.1 (medium), 12.7 (strong), 13.8 (medium), 14.4 (very weak), 15.0 (medium), 15.9 (medium), 16.6 (weak), 17.8 (weak), 18.3 (very weak), 18.7 (very weak), 19.0 (very weak), 20.1 (medium), 21.0 (weak), 21.8 (medium), 22.9 (medium), 23.6 (medium), 24.7 (weak), 25.7 (medium), 27.4 (weak), 28.0 (weak), 29.5 (very weak), by successively reacting cyanuric chloride with 4,4'-diaminostilbene disulphonic acid di-sodium salt, aniline and diethanolamine, adjusting the pH of the mixture to 9.0 to 9.5 with concentrated sodium hydroxide solution and evaporating the mixture to dryness.

2. A process for the production of
the (C) hydrate crystal form in which x represents 14 to 20 and characterized by an X-ray diffraction gattem which shows absorptions in the 2Ø-area between 1° and 30° as follows:
6.4 (strong), 6.6 (strong), 7.9 (weak), 9.3 (medium), 11.1 (strong), 11.9 (very weak), 12.7 (weak), 13.2 (very weak), 14.7 (very weak), 15.2 (very weak), 15.7 (weak), 16.0 (very weak), 16.5 (weak), 17.1 (weak), 17.6 (very weak), 18.7 (very weak), 19.8 (weak), 20.6 (medium), 21.1 (medium), 21.8 (weak), 22.3 (strong), 22.5 (medium), 23.9 (weak), 24.2 (very weak), 25.0 (very weak), 25.8 (very strong), 26.4 (medium), 27.2 (weak), 28.1 (medium), 29.2 (weak), by neutralization of the free acid of the 4,4'-di-triazinylamino-2,2'-di-sulfostilbene possessing the (A) hydrate form according to claim 1 with dilute sodium hydroxide solution, homogenising and allowing to stand at room temperature;

the (D) hydrate crystal form in which x represents 10 to 14 and characterized by an X-ray diffraction pattern which shows absorptions in the 2Ø-area between 1° and 30° as follows:
4.9 (very strong), 6.9 (very weak), 9.7 (very weak), 10.8 (very weak), 12.3 (medium), 12.8 (medium), 13.8 (medium), 14.2 (medium), 14.5 (strong), 15.0 (weak), 15.6 (very weak), 15.9 (very weak), 16.2 (very weak), 16.5 (weak), 17.5 (very weak), 18.2 (very weak), 19.1 (very weak), 19.8 (very weak), 20.2 (weak), 20.8 (very weak), 21.4 (weak), 21.8 (medium), 22.4 (medium), 23.1 (medium), 24.4 (medium), 25.2 (medium), 26.7 (weak), 27.7 (very weak), 28.6 (medium), by treatment of the sodium salt of the 4,4'-di-triazinylamino-2,2'-di-sulfostilbene possessing the (A) hydrate form according to claim 1 with aqueous sodium chloride solution, stabilizing and homogenising; and the (E) hydrate crystal form in which x represents 16 to 26 and characterized by an X-ray diffraction pattern which shows absorptions in the 2∅-area between 1° and 30° as follows:

5.0 (very strong), 5.8 (weak), 7.1 (very weak), 9.8 (weak), 10.3 (weak), 10.9 (weak), 11.4 (weak), 12.4 (medium), 12.8 (medium), 13.9 (strong), 14.4 (strong), 14.6 (very strong), 15.0 (medium), 15.7 (very weak), 16.6 (very weak), 17.5 (very weak), 19.3 (weak), 20.3 (weak), 20.9 (weak), 21.4 (weak), 21.9 (medium), 22.7 (weak), 23.3 (weak), 24.3 (medium), 24.6 (medium), 25.3 (medium), 25.9 (weak), 26.9 (weak), 27.8 (medium), 28.7 (strong), 29.2 (weak), by treatment of the free acid of 4,4'-di-triazinylamino-2,2'-di-sulfostilbene possessing the (A) hydrate form according to claim 1 with concentrated sodium hydroxide solution and homogenising.

3. A process for the production of a mixture of two or more of the hydrates of formula (I), according to claim 1, which comprises mixing an aqueous solution of sodium chloride or sodium sulfate and a hydrate of formula (I), according to claim 1.

4. A process according to claim 3 in which the inorganic electrolyte is an alkali metal halide or sulfate.

5. A process according to claim 4 in which the alkali metal halide or sulfate is sodium chloride or sodium sulfate, or a mixture thereof.

6. A process according to claim 3 to which comprises a) firstly preparing an aqueous solution of the electrolyte, b) seeding this electrolyte solution with a previously-prepared sample of the active substance of formula (I), obtained according to claim 3, and, while maintaining the pH value of the seeded electrolyte solution within the range of from 7.5 to 9.0, c) adding the active substance of formula (I), as the free acid, alkali, and water, simultaneously and portionwise, to the seeded electrolyte solution.

7. A process according to claim 6 in which, in step b), the pH value of the seeded electrolyte solution is maintained within the range of from 8.0 to 8.5.

8. A process according to claim 6 in which, in step c), the alkali is sodium hydroxide.

9. A process according to claim 3 in which water and the free acid form of the a hydrate of formula (I) are mixed until a) the content of the hydrate in the synthesis mixture is within the range of from 5 to 40% by weight and b) the content of electrolyte in the synthesis mixture is within the range of from 0.5 to 2.5% by weight.

10. A process according to claim 9 in which water and the free acid form of the hydrate are mixed until a) the content of the active substance in the synthesis mixture is within the range of from 10 to 30% and b) the content of electrolyte in the synthesis mixture is within the range of from 1 to 2% by weight.

11. A process according to claim 9 in which water and the free acid form of the hydrate are mixed until a) the content of the active substance in the synthesis mixture is within the range of from 15 to 25% by weight and b) the content of electrolyte in the synthesis mixture is about 1.5% by weight.

12. A process according to claim 6 in which the seed crystals are used in the form of small crystals whose average size does not markedly exceed 10 microns.

13. A process according to claim 12 in which the amount of seed crystal added is between 0.1 and 60% by weight, relative to the total hydrate content.

14. A process according to claim 13 in which the amount of seed crystal added is between 1 and 50% by weight, relative to the total hydrate content.

15. A process according to claim 14 in which the amount of seed crystal added is between 1 and 30% by weight, relative to the total hydrate content.

16. A process according to claim 3 in which the reaction temperature for preparing the mixtures of hydrate of formula (I) lies within the range of from 10–95° C.

17. A process according to claim 16 in which the reaction temperature for preparing the mixtures of hydrate of formula (I) lies within the range of from 35–55° C.

18. A process for the production of the (F) form of the 4,4'-di-triazinylamino-2,2'-di-sulfostilbene compound having the formula:

in which M and $M_1$ are hydrogen and x represents 4 to 10 and characterized by an X-ray diffraction pattern which shows absorptions in the 2∅-area between 1° and 30° as follows:

5.7 (very strong), 6.4 (very weak), 10.1 (medium), 11.3 (very strong), 14.9 (weak), 17.0 (very weak), 19.5 (weak), 21.3 (weak), 22.6 (medium), 23.9 (very weak), 24.7 (weak), 25.7 (weak), 26.8 (weak), 28.4 (weak), by acidifying the sodium salt of the 4,4'-di-triazinylamino-2,2'-di-sulfostilbene according to claim 1 with hydrochloric acid and filtering the precipitated product.

19. A process for the production of a 4,4'-di-triazinylamino-2,2'-di-sulfostilbene compound in having the formula:

which M and $M_1$ both represent potassium and in which x represents 9 to 17, the hydrate being characterized by an X-ray diffraction pattern which shows absorptions in the 2∅-area between 1° and 30° as follows:

4.7 (very strong), 7.0 (very weak), 9.5 (very weak), 10.5 (very weak), 10.9 (weak), 12.1 (medium), 12.6 (medium), 13.1 (very weak), 13.9 (medium), 14.2 (strong), 15.1(weak), 16.3 (very weak), 17.5 (very weak), 19.0 (very weak), 19.4 (very weak), 20.2 (weak), 21.0 (very weak), 21.4 (very weak), 21.9 (medium), 22.2 (very weak), 22.5 (weak), 23.1 (weak), 24.5 (weak), 24.8 (weak), 25.2 (medium), 26.1 (weak), 26.5 (weak), 26.8 (very weak), 28.1 (weak), 28.9 (strong), 29.6 (very weak), by neutralizing the free acid form of said 4,4'-di-triazinylamino-2,2'-di-sulfostilbene with potassium hydroxide.

20. A process for the production of a 4,4'-di-triazinylamino-2,2'-di-sulfostilbene compound having the formula:

in which M and $M_1$ both represent lithium and in which x represents 9 to 30, the hydrates being characterized by an X-ray diffraction pattern which shows absorptions in the 2Ø-area between 1° and 30° as follows:

3.3 (medium), 3.4 (medium), 3.6 (medium), 5.6 (very weak), 5.9 (very weak), 6.5 (very strong), 6.8 (medium), 7.2 (strong), 8.8 (medium), 9.4 (very weak), 9.5 (very weak), 9.7 (very weak), 10.2 (ry weak), 10.8 (weak), 11.2 (very weak), 11.6 (very weak), 12.0 (medium), 13.0 (very weak), 16.2 (medium), 17.1 (weak), 17.4 (very weak), 17.8 (weak), 18.0 (weak), 18.7 (weak), 19.2 (very weak), 19.9 (medium), 20.1 (medium), 20.6 (weak), 21.1 (weak), 21.6 (very weak), 22.1 (weak), 22.6 (weak), 23.0 (very weak), 23.3 (very weak), 23.4 (very weak), 23.8 (weak), 24.1 (weak), 24.4 (very weak), 25.0 (weak), 25.3 (weak), 25.7 (weak), 27.8 (very weak), 28.3 (weak), or 3.2 (weak), 6.4 (medium), or 6.4 (strong), 7.8 (very weak), 9.3 (weak), 11.0 (weak), 11.8 (very weak), 12.9 (very weak), 14.7 (very weak), 15.2 (very weak), 15.8 (very weak), 16.6 (weak), 17.4 (weak), 18.3 (very weak), 18.7 (very weak), 19.3 (very weak), 19.9 (very weak), 20.5 (medium), 21.1 (weak), 21.8 (weak), 22.2 (medium), 22.7 (medium), 24.1 (medium), 25.9 (medium), 26.5 (very weak), 27.0 (weak), 27.9 (weak), 28.5 (weak), 28.9 (very weak), or a mixture containing two or more of the hydrates of said 4,4'-di-triazinylamino-2,2'-di-sulfostilbene compound, by neutralizing the free acid form of said 4,4'-di-triazinylamino-2,2'-di-sulfostilbene with lithium hydroxide.

* * * * *